United States Patent [19]

Downs et al.

[11] Patent Number: 4,540,780

[45] Date of Patent: Sep. 10, 1985

[54] DIPHENYLMETHYLENE PIPERIDINES

[75] Inventors: David A. Downs; Haile Tecle, both of Ann Arbor, Mich.

[73] Assignee: Warner-Lambert Company, Morris Plains, N.J.

[21] Appl. No.: 500,344

[22] Filed: Jun. 2, 1983

[51] Int. Cl.$^3$ .................. C07D 413/06; C07D 401/06; C07D 417/06
[52] U.S. Cl. ...................... 544/129; 544/60; 544/360; 546/165; 546/191; 546/208
[58] Field of Search .................. 544/129, 360, 60; 546/165, 191, 208

[56] References Cited

U.S. PATENT DOCUMENTS 3,036,080  5/1962  Barry .................. 546/191

*Primary Examiner*—Robert W. Ramsuer
*Attorney, Agent, or Firm*—Ronald A. Daignault

[57] ABSTRACT

Novel chemical compounds which are diphenylmethylene piperidine compounds are provided, as well as methods for their production, pharmaceutical compositions comprising the compounds, and methods of treatment using the compounds in dosage form. The compounds have both anticholinergic and antidopaminergic properties, and are useful as antiemetic, antihistamine, pulmonary, antiallergy, and antispasmodic agents.

3 Claims, No Drawings

DIPHENYLMETHYLENE PIPERIDINES

TECHNICAL FIELD

The invention relates to novel diphenylmethylene piperidine compounds, to methods for their production, to pharmaceutical compositions comprising the compounds, and to methods of treatment using the compounds in dosage form. The compounds of the invention have both anticholinergic and antidopaminergic properties, and are useful as antiemetic, antihistamine, pulmonary, antiallergy and antispasmodic agents.

SUMMARY OF THE INVENTION

The invention in one aspect relates to novel chemical compounds, namely diphenylmethylene piperidine compounds having, in free base form, the structural

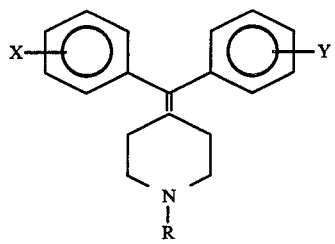

where R has the structural formula Ia, Ib, Ic, Id, Ie or If:

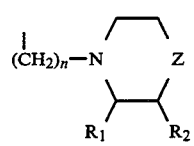   Ia

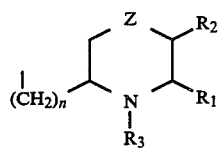   Ib

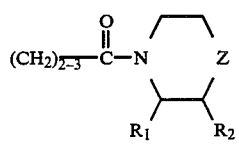   Ic

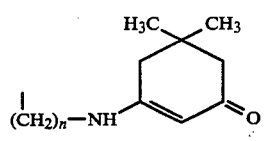   Id

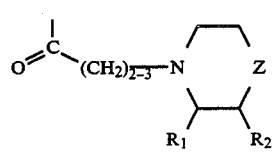   Ie

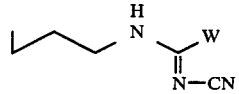   If and where X and Y, which can be the same or different, are H, halogen, halomethyl, alkyl or alkoxy; n is 2, 3 or 4; Z is O, $CH_2$, S, single bond, =C-fluorophenoxy, =CHOH, =$CHCH_2CH_2OH$, =$C(OH)_2$, or $NR_4$, $R_4$ being H, alkyl, or aryl; $R_1$ and $R_2$, which can be the same or different, are H, alkyl, or an aromatic or heteroaromatic ring; W is $SCH_3$, $NHCH_3$ or 1-piperidinyl; an $R_3$ is H, alkyl, aryl, or aralkyl; and pharmaceutically acceptable salts thereof.

The compounds of the invention form pharmaceutically acceptable salts with both organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic, lactic, gluconic, glucuronic, sulfamic, benzoic, tartaric, pamoic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms with pharmaceutically acceptable solvents such as water, ethanol and the like are equivalent to the unsolvated forms for purposes of the invention. The compounds can exist as optical and geometric isomers; such isomers are included within the scope of the invention.

The invention in a preferred aspect relates to diphenylmethylene piperidine compounds having in free base form the structural formula A:

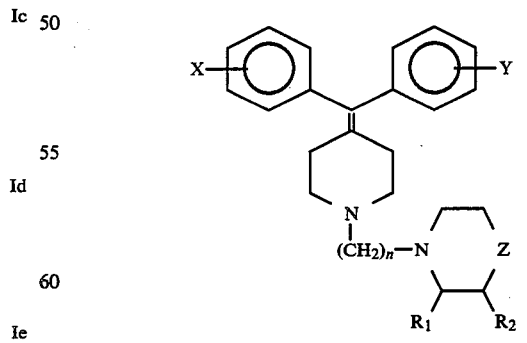

and pharmaceutically acceptable salts thereof, where n, $R_1$, $R_2$, X, Y, and Z have the above meaning.

The invention in another preferred aspect relates to diphenylmethylene piperidine compounds having in free base form the structural formula B:

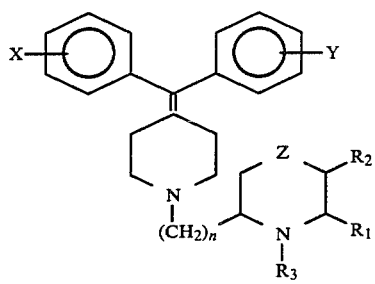

and pharmaceutically acceptable salts thereof, where n, $R_1$, $R_2$, $R_3$, X, Y, and Z have the above meaning.

The invention in another preferred aspect relates to diphenylmethylene piperidine compounds having in free base form the structural formula C:

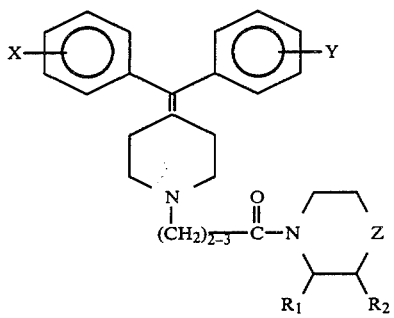

and pharmaceutically acceptable salts thereof, where $R_1$, $R_2$, X, Y, and Z have the above meaning.

The invention in another preferred aspect relates to diphenylmethylene piperidine compounds having in free base form the structural formula D:

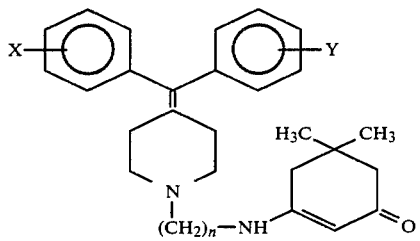

and pharmaceutically acceptable salts thereof, where n, X, and Y have the above meaning.

The invention in another preferred aspect relates to diphenylmethylene piperidine compounds having in free base form the structural formula E:

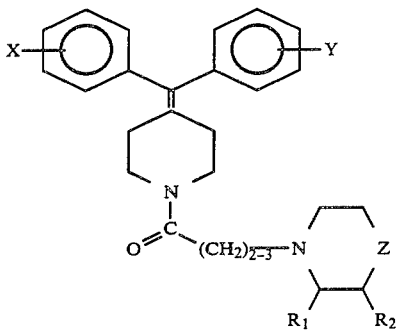

and pharmaceutically acceptable salts thereof, where $R_1$, $R_2$, X, Y and Z have the above meaning.

The invention in another preferred aspect relates to diphenylmethylene piperidine compounds having in free base form the structural formula F:

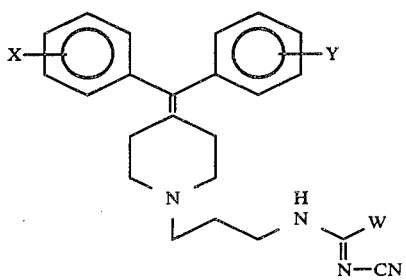

and pharmaceutically acceptable salts thereof, where W, X and Y have the above meaning.

Preferred compound species, for purposes of the invention are the following:

Morpholine, 4-[2-[4-(diphenylmethylene)-1-piperidinyl]ethyl]-;
Piperidine, 4-(diphenylmethylene)-1-[2-(1-pyrrolidinyl)ethyl]-;
Piperidine, 4-(diphenylmethylene)-1-[2-(1-piperidinyl)ethyl]-;
Piperidine, 4-(diphenylmethylene)-1-[3-(1-piperidinyl)propyl]-;
Piperidine, 4-(diphenylmethylene)-1-[2-(1-methyl-2-pyrrolidinyl)ethyl]-;
Quinoline, 1-[3-[4-(diphenylmethylene)-1-piperidinyl]propyl]-1,2,3,4-tetrahydro-;
4-Piperidinol, 1-[3-[4-(diphenylmethylene)-1-piperidinyl]propyl]-;
4-Piperidineethanol, 1-[3-[4-(diphenylmethylene)-1-piperidinyl]propyl]-;
Piperidine, 4-(diphenylmethylene)-1-[4-(1-piperidinyl)butyl]-;
Piperidine, 1-[3-(1-piperidinyl)propyl]-4-[bis(4-fluorophenyl)methylene]-;
Piperidine, 4-[bis-(4-fluorophenyl)-methylene]-1-[2-(1-piperidinyl)ethyl]-;
Piperidine, 4-[bis-(4-fluorophenyl)-methylene]-1-[2-(1-methyl-2-pyrrolidinyl)ethyl]-;
Piperidine, 4-[bis-(3-fluorophenyl)-methylene]-1-[3-(1-piperidinyl)propyl]-;
Piperidine, 4-[(3-chlorophenyl)phenylmethylene]-1-[3-(1-piperidinyl)propyl]-;

Piperidine, 4-[(3-fluorophenyl)phenylmethylene]-1-[3-(1-piperidinyl)propyl]-;

Quinoline, 1-[3-[4-(diphenylmethylene)-1-piperidinyl]-1-oxopropyl-1,2,3,4-tetrahydro-;

Pyridine, 1-[3-[4-(diphenylmethylene)-1-piperidinyl]-1-oxopropyl]-3-(4-fluorophenoxy)-1,2,3,6-tetrahydro-;

2-Cyclohexen-1-one, 3-[[2-[4-(diphenylmethylene)-1-piperidinyl]ethyl]amino]-5.5-dimethyl;

4,4-Piperidinediol, 1-[3-[4-(diphenylmethylene)-1-piperidinyl]-1-oxopropyl];

Piperidine, 4-(diphenylmethylene)-1-[1-oxo-3-(piperidinyl)propyl]-;

Piperidine, 4-(diphenylmethylene)-1-[1-oxo-4-(1-piperidinyl)butyl]-;

Carbamimidothioic acid, N'-cyano-N-[3-[4-(diphenylmethylene)-1-piperidinyl]-propyl]-, methyl ester;

Guanidine, N'-cyano-N-[3-[4-(diphenylmethylene)-1-piperidinyl]propyl]-N'-methyl;

1-Piperidinecarboximidamine, N'-cyano-N-[3-[4-(diphenylmethylene)-1-piperidinyl]propyl]; and the pharmaceutically acceptable salts thereof.

Also preferred, particularly for their antiemetic properties when formulated in pharmaceutical dosage form, are morpholine, 4-[2-[4-(diphenylmethylene)-1-piperidinyl]ethyl]-, and pharmaceutically acceptable salts thereof.

PROCESS FOR PREPARING THE COMPOUNDS

The invention in one process aspect comprises a process for preparing compounds having in free base form the structural formula II:

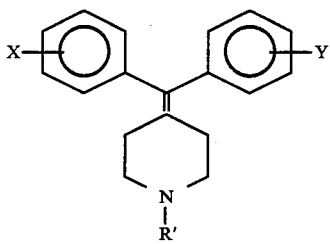

II comprising dehydrating a compound having the structural formula III:

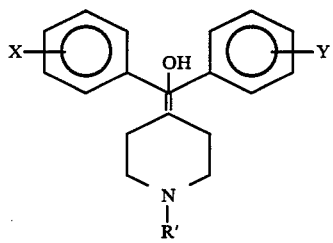

III in the presence of an acid medium, and isolating the product in free base form or acid addition salt form; where X and Y have the above meaning and R' has the above structural formula Ia or Ib. The reaction can be carried out in any suitable way. Preferably, the piperidine methanol starting material is dissolved in aqueous acid and the solution subjected to reflux for a short period. The product is isolated conveniently as the acid addition salt.

In another embodiment, the invention comprises a process for preparing compounds having in free base form the structural formula IV:

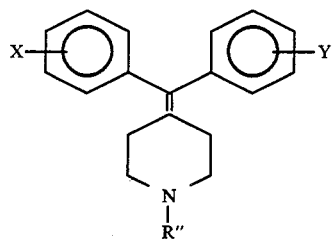

IV comprising reacting a compound having the structural formula V:

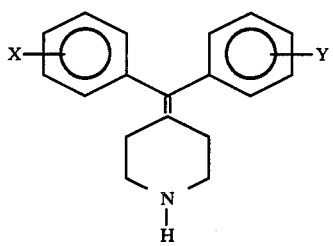

V with a compound of formula Hal—R" and isolating the product in free base form or acid addition salt form; where X and Y have the above meaning, R" has the above structural formula Ia, Ib, Ic, Id or Ie, and Hal is a halogen atom. The reaction is ordinarily carried out in solvent such as ethanol in the presence of an acid scavenger such as sodium bicarbonate, conveniently at room temperature or higher temperature up to reflux temperature.

In another embodiment, the invention comprises a process for preparing compounds having in free base form the structural formula VI:

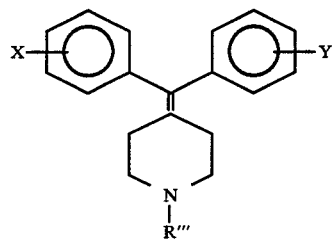

VI comprising subjecting to reduction a compound having the structural formula VII:

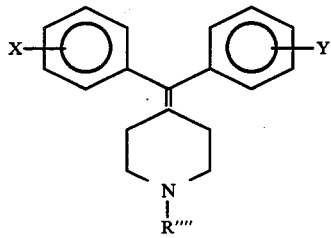

VII and isolating the product in free base form or acid addition salt form; where R''' and R'''' respectively have the structural formulas Ia and Ic or Ie, and n is 3 or 4. The reduction may be accomplished with a selective reducing agent such as lithium aluminum hydride in an unreactive solvent such as tetrahydrofuran.

In another embodiment the invention relates to a process for preparing compounds having in free base form the structural formula VIII:

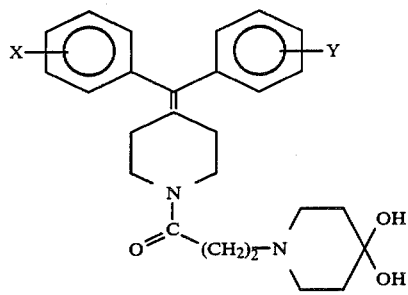

comprising subjecting to hydrolysis a compound having the structural formula IX:

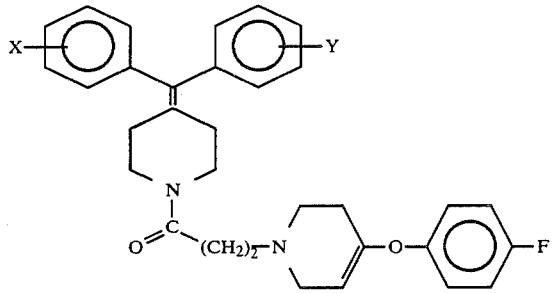

in the presence of an acid medium, and isolating the product in free base form or acid addition salt form; where X and Y have the above meaning.

In another embodiment the invention relates to a process for preparing compounds having in free base form the structural formula XII:

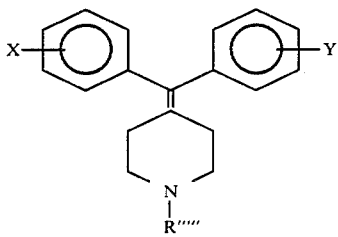

comprising reacting a compound having the structural formula XIII:

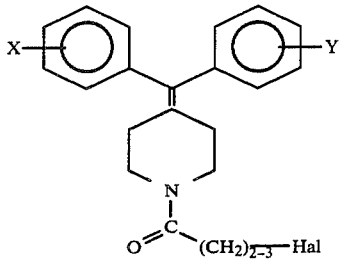

with a compound having the structural formula XIV:

and isolating the product in free base form or acid addition salt form; where $R_1$, $R_2$, X, Y, and Z have the above meaning, Hal is a halogen atom, and R''''' has the above structural formula Ie.

In still another embodiment the invention relates to a process for preparing compounds having in free base form the structural formula X:

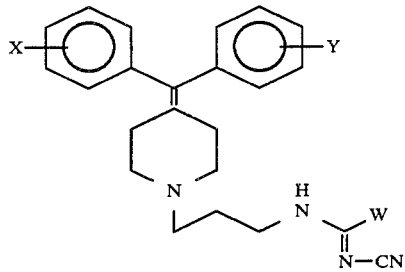

comprising reacting a compound having the structural formula XI:

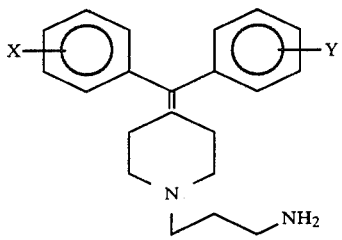

with dimethyl cyanocarbonimidiodithioate to produce a first product where W is $SCH_3$, and where desired, reacting the first product with methylamine or piperidine to product a second product where respectively, W is $NHCH_3$ or 1-piperidinyl, and isolating the product in free base form or acid addition salt form; where W, X, and Y have the above meaning.

The starting materials for the process embodiments of the invention are either known materials or can be made by the illustrative procedures described below in detail. Purification of compounds or products obtained by the methods of the invention is accomplished in any suitable way, preferably by column chromatography or crystallization.

PHARMACEUTICAL COMPOSITIONS

The invention in its composition aspect relates to a pharmaceutical composition comprising a free base compound having the above generic or subgeneric structural formulas I, A, B, C, D, E or F, or a pharmaceutically acceptable salt thereof, in combination with a pharmaceutically acceptable carrier.

The invention in another aspect relates to a pharmaceutical composition comprising a compound having structural formula I where R has the structural formula Ia, or a pharmaceutically acceptable salt thereof in combination with a pharmaceutically acceptable carrier.

METHOD FOR TREATING MAMMALS

The invention in another method aspect relates to a method for treating pulmonary, allergic, and/or spasmodic disorder in a mammal which comprises administering a sufficient amount of a compound having structural formula I and the pharmaceutically acceptable salts thereof in combination with a pharmaceutically acceptable carrier, to a mammal in need thereof.

The invention in another method aspect relates to a method for treating nausea and/or emesis, in a mammal which comprises administering a sufficient amount of compound having structural formula I and the pharmaceutically acceptable salts thereof in combination with a pharmaceutically acceptable carrier, to a mammal in need thereof.

PHYSICAL AND PHARMACOLOGICAL PROPERTIES OF THE COMPOUNDS

The diphenylmethylene piperidine compounds of the invention range in color from beige to orange. They are crystalline solids that are stable under normal atmospheric conditions. The compounds typically have melting points in the range of about 100° to about 250° C.

As indicated, the compounds are useful as pharmacological agents for the treatment of pulmonary, allergic, and/or spasmodic disorder and of nausea and/or emesis in warm-blooded animals. The activity of representative compounds of the invention was established by test protocols described below.

TEST PROTOCOLS

1. ANTICHOLINERGIC MUSCARINIC RECEPTOR BINDING ASSAY METHOD

This test uses the displacement of [$^3$H]quinuclindinyl benzilate ([$^3$H]QNB)(MRBA) from specific muscarinic cholinergic receptors in the rat brain to measure in vitro anticholinergic activity of compounds. A brain tissue homogenate is prepared from whole rat bran excluding the cerebellum and lower brain stem. A Long-Evans male rat weighing 180–200 grams is routinely used. The brain tissue homogenate along with appropriate concentrations of test compounds and [$^3$H]QNB is incubated for one hour at 25° C. in a buffer medium of 50 mM Na-K PO$_4$ pH 7.4. The material is filtered and washed on a millipore filter using Whatman GF/B filters. The filters are counted on a scintillation spectrophotometer. A maximal displacement by 0.1 mM oxotremorine is used to determine how much of the total binding is specific for muscarinic receptors.

Results: The results are reported as percent inhibition of total specific binding. Reference: Yamamura, Henry L. and Synder, Solomon H. (1974). Muscarinic Cholinergic Binding in Rat Brain Proc. Nat. Acad. Sci. USA Vol 71 No. 5 pp. 1725–1729 May 1974.

2. HALOPERIDOL RECEPTOR BINDING ASSAY

Purpose: The inhibition of $^3$H-Haloperidol binding (HRBA) for brain dopamine receptors by various neuroleptics has a good correlation with the available clinical potencies of neuroleptics.

Rat corpus striatum is homogenized in 50 mM tris buffer (pH7.7) and centrifuged. Pellets are rehomogenized in the same buffer and used for binding assay. Test drug is incubated with 0.6 nM $^3$H-haloperidol and brain tissue in vitro. After incubation, it is filtered with glass fiber filter and washed. The tissue bound $^3$H-haloperidol in the filter is counted in scintillation fluid.

One nM and 10 nM of test drug is used in triplicate in the primary screen. More concentrations of test drug are used for the calculation of 50 percent inhibition (IC)$_{50}$.

The compound with 60 to 100 percent inhibition is designated as active to very active (A), with 30 to 50 percent inhibition as moderate to active (C) and with 0 to 30 percent as not active (N).

3. APOMORPHINE EMESIS ASSAY

Method: Dogs, unsegregated with respect to breed or sex, are used. They are fasted for 16 hours prior to the administration of the test compound. The test compounds are given orally by stomach tube at intervals prior to a subcutaneous injection of 0.1 mg/kg of apomorphine hydrochloride. The dogs are observed for changes in behavior or signs of neuropharmacologic action during the period between drugs and the emetic. After the apomorphine injection the frequency of vomiting episodes is recorded.

The number of dogs vomiting per total number tested, the number of vomiting episodes for each dog, and the average number of episodes are reported for dogs treated with the test compound and dogs treated with vehicle.

The drug is rated as being active if no vomiting episodes are seen in 50 percent or more of the dogs tested.

These test protocol procedures gave results listed in Tables 1 and 2 for representative compounds of the invention.

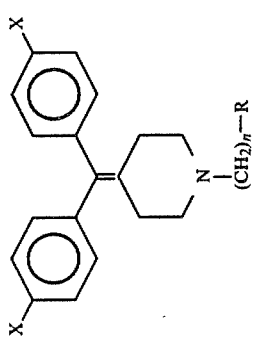

TABLE 1

Pharmacological, Physical, and Analytical Data

| CPD No | n | x | y | R | MRBA | HRBA | mp °C. | Recryst Solvent | Formula | Analysis Calcd. C | H | N | Found C | H | N |
|---|---|---|---|---|---|---|---|---|---|---|---|---|---|---|---|
| 1 | 2 | H | | ![morpholine]N-/O | IC$_{50}$ = 148 nM | IC$_{50}$ = 29 nM | ≧285 | EtOH—H$_2$O | C$_{24}$H$_{30}$N$_2$O.2HCl | 66.20 | 7.41 | 6.44 | 66.02 | 7.65 | 6.51 |
| 2 | 2 | H | | ![pyrrolidine]N- | IC$_{50}$ = 8.4 nM | IC$_{50}$ = 309 | 280 (dec) | EtOH—H$_2$O | C$_{24}$H$_{30}$N$_2$.2HCl | 68.72 | 7.64 | 6.68 | 68.52 | 7.62 | 6.55 |
| 3 | 2 | H | | ![piperidine]N- | IC$_{50}$ = 18.1 nM | IC$_{50}$ = 135 nM | 310 (dec) | EtOH | C$_{25}$H$_{32}$N$_2$.2HCl.¼H$_2$O | 68.56 | 7.94 | 6.40 | 68.52 | 8.08 | 6.26 |
| 4 | 3 | H | | ![piperidine]N- | IC$_{50}$ = 15 nM | IC$_{50}$ = 50.4 nM | 293-295 | EtOH | C$_{26}$H$_{34}$N$_2$.2HCl.¼H$_2$O | 68.40 | 8.17 | 6.14 | 68.67 | 8.14 | 6.04 |
| 5 | 2 | H | | ![N-methylpyrrolidine]N-CH$_3$ | IC$_{50}$ = 19.9 nM | IC$_{50}$ = 72.7 | 270-273 | EtOH—acetone | C$_{25}$H$_{32}$N$_2$.2HCl.½H$_2$O | 67.85 | 7.97 | 6.33 | 67.72 | 7.78 | 6.21 |

TABLE 1-continued

Pharmacological, Physical, and Analytical Data

| CPD No | n | x | y | R | MRBA | HRBA | mp °C. | Recryst Solvent | Formula | Calcd. C | Calcd. H | Calcd. N | Found C | Found H | Found N |
|---|---|---|---|---|---|---|---|---|---|---|---|---|---|---|---|
| 6 | 4 | H | | piperidine (—N⟨piperidine⟩) | 83 | | | | | | | | | | |
| 7 | 2 | H | | 3,4-dihydroquinolin-1(2H)-yl carbonyl | 52 | | | Et₂O | C₃₀H₃₂N₂O·HCl | 75.39 | 7.04 | 5.87 | 75.48 | 7.08 | 5.80 |
| 8 | 3 | H | | 4-(4-fluorophenoxy)-3,6-dihydro-2H-pyridin-1-yl carbonyl | 64 | | | | | | | | | | |
| 9 | 2 | H | | 5,5-dimethyl-3-amino-cyclohex-2-enone | 73 | 63 | 171–172 | Et₂O | C₂₈H₃₄N₂O | 81.12 | 8.27 | 6.76 | 81.07 | 7.73 | 6.84 |
| 10 | 3 | H | | 3,4-dihydroquinolin-1(2H)-yl | 83 | 69 | 110 (dec) | EtOH | C₃₀H₃₄N₂·2HCl·H₂O | 70.16 | 7.46 | 5.49 | 70.40 | 7.53 | 5.61 |
| 11 | 2 | H | | 4,4-dihydroxypiperidin-1-yl carbonyl | IC₅₀ = 38.3 nM | IC₅₀ = 367 nM | 108–110 | Et₂O | C₂₆H₃₂N₂O₃ | 74.25 | 7.67 | 6.66 | 74.49 | 7.39 | 6.50 |

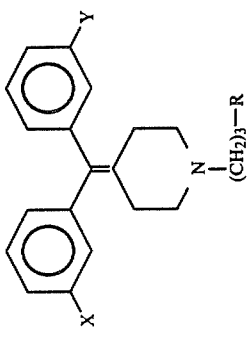

TABLE 1-continued

Pharmacological, Physical, and Analytical Data

| CPD No | n | x | y | R | MRBA | HRBA | mp °C. | Recryst Solvent | Formula | Calcd. C | Calcd. H | Calcd. N | Found C | Found H | Found N |
|---|---|---|---|---|---|---|---|---|---|---|---|---|---|---|---|
| 12 | 3 | H | | ![piperidine-4-OH] | 63 | 89 | 267 (dec) | | $C_{26}H_{34}N_2O \cdot 2HCl \cdot \frac{1}{2}H_2O$ | 66.09 | 7.89 | 5.93 | 66.38 | 8.04 | 5.87 |
| 13 | 3 | H | | ![piperidine-4-CH2CH2OH] | 83 | 55 | 115 (dec) | | $C_{28}H_{35}N_2O \cdot 2HCl \cdot H_2O$ | 66.00 | 8.31 | 5.50 | 66.18 | 7.56 | 5.40 |
| 14 | 3 | F | | ![piperidine] | 57 | 73 | 284–287 | EtOH | $C_{28}H_{32}F_2N_2 \cdot 2HCl \cdot \frac{1}{2}H_2O$ | 63.41 | 7.16 | 5.69 | 63.50 | 7.00 | 5.56 |
| 15 | 2 | F | | ![piperidine] | 67 | 62 | 268 (dec) | EtOH | $C_{25}H_{30}F_2N_2 \cdot 2HCl$ | 63.96 | 6.87 | 5.97 | 64.44 | 6.80 | 5.84 |
| 16 | 2 | F | | ![N-methylpyrrolidine] | 36 | 48 | 163 (dec) | Acetone | $C_{25}H_{30}F_2N_2 \cdot 2C_4H_4O_4$ | 63.04 | 6.09 | 4.46 | 63.00 | 6.04 | 4.08 |

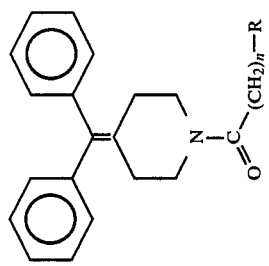
TABLE 1-continued
Pharmacological, Physical, and Analytical Data
| CPD No | n | x | y | R | MRBA | HRBA | mp °C. | Recryst Solvent | Formula | Calcd. C | Calcd. H | Calcd. N | Found C | Found H | Found N |
|---|---|---|---|---|---|---|---|---|---|---|---|---|---|---|---|
| 17 | | F | F | piperidine | 32 | | | | | | | | | | |
| 18 | | Cl | H | piperidine | 37 | 52 | 300–304 | MeOH | $C_{26}H_{33}ClN_2 \cdot HCl$ | 64.80 | 7.32 | 5.81 | 64.93 | 7.38 | 5.77 |
| 19 | | F | H | piperidine | 45 | 36 | 299–204 | MeOH | $C_{26}H_{33}FN_2 \cdot HCl$ | 67.09 | 7.58 | 6.02 | 66.79 | 7.73 | 5.97 |
| 20 | 2 | | | piperidine | 54 | | | | | | | | | | |

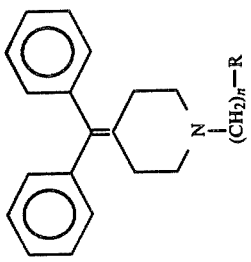
TABLE 1-continued
Pharmacological, Physical, and Analytical Data
| CPD No | n | x | y | R | MRBA | HRBA | mp °C. | Recryst Solvent | Formula | Analysis Calcd. C | H | N | Found C | H | N |
|---|---|---|---|---|---|---|---|---|---|---|---|---|---|---|---|
| 21 | 3 | | | NH—C(=CN)—SCH₃ | IC₅₀ = 64.7 nM | IC₅₀ = 39.2 nM | 161-164 | | C₂₄H₂₈N₄S | 71.25 | 6.98 | 13.85 | 71.20 | 6.84 | 13.75 |
| 22 | 3 | | | NH—C(=CN)—NHCH₃ | 42 | 73 | 180-181 | | C₂₄H₂₉N₅ | 74.38 | 7.54 | 18.07 | 74.53 | 7.35 | 18.07 |
| 23 | 3 | | | NH—C(=CN)—N(piperidine) | 86 | 55 | 138-141 | | C₂₈H₃₅N₅ | 76.15 | 7.99 | 15.86 | 75.66 | 8.22 | 15.48 |

These results show that representative compounds of the invention, designated by compound number and so referenced in the preparative examples which follow, possess significant activity in the MRBA and HRBA test procedures described above.

A preferred morpholine compound of the invention, namely, morpholine, 4-[2-[4-diphenylmethylene)-1-piperidinyl]ethyl], dihydrochloride, (designated hereinafter as Compound 1), shows significant antiemetic properties in the apomorphine enesis assay described above, with an $ED_{50}$ of about 5.0 mg./kg. oral. In general, active compounds with multiple antidopaminergic ($D_2$), antihistaminic ($H_1$), and antimuscarinic actions are considered in the art to be superior agents against nausea and emesis resulting from a variety of stimuli affecting vestibular (motion sickness), medullary (chemotherapy), and chemoreceptor trigger zone centers. In this regard, as a demonstration of significant activity, the following Table 2 shows the relative affinities of representative compounds of the invention.

TABLE 2

Affinities of a Series of Diphenylmethylenepiperidines for Dopamine $D_2$, Muscarinic and Histamine $H_1$ Receptors in Rat Brain Membrane

| Compound No. | n | R | X | Receptor $K_1$ (nM) Dopamine $D_2$ | Muscarinic Cholinergic | Histamine* $H_1$ |
|---|---|---|---|---|---|---|
| 3 | 2 | —N(piperidinyl) | H | 105 | 3 | 12 |
| 15 | 2 | —N(piperidinyl) | F | 56 | 17 | 86 |
| 13 | 3 | —N(piperidinyl)—$(CH_2)_2OH$ | H | 158 | 5 | 19.5 |
| 9 | 2 | —NH—(4,4-dimethylcyclohex-2-en-1-one) | H | 75 | 11 | 56 |
| 14 | 3 | —N(piperidinyl) | F | 67 | 23 | 16 |
| 12 | 3 | —N(piperidinyl)—OH | H | 25 | 15 | 6.1 |
| 10 | 2 | —N(morpholino) | H | 31 | 32 | 20 |

TABLE 2-continued

Affinities of a Series of Diphenylmethylenepiperidines for Dopamine D$_2$, Muscarinic and Histamine H$_1$ Receptors in Rat Brain Membrane

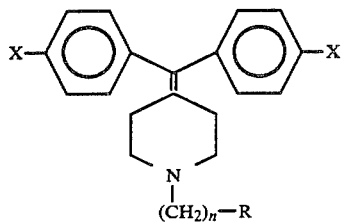

| Compound No. | n | R | X | Receptor K$_1$ (nM) Dopamine D$_2$ | Muscarinic Cholinergic | Histamine* H$_1$ |
|---|---|---|---|---|---|---|
| — | 3 | —N⟨tetrahydroquinoline⟩ | H | 42 | 11 | 31 |
| 21 | 3 | —N=CSCH$_3$, NHCN | H | 32 | 8.6 | 0.38 |
| 23 | 3 | —N=C—N⟨piperidine⟩, NHCN | H | 28 | 2 | 1.7 |

*Tran V. T., Lebovitz, R., Toll, L., and Snyder, S. H.: [$^3$H]—Doxepin interactions with histamine H$_1$—receptors in guinea pig and rat brain homogenates. Eur J Pharmacol 70:501–509, 1981

PREPARATION OF PHARMACEUTICAL COMPOSITIONS

When being utilized as pharmaceutical agents, the compounds of the invention can be prepared and administered in a wide variety of topical, oral, and parenteral dosage forms. It will be clear to those skilled in the art that the following dosage forms may comprise as the active component, one or more compounds of formula 1, a corresponding pharmaceutically acceptable salt of any of said compounds, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or snythetic gums, resins, methyl cellulose, sodium carboxymethyl cellulose, and other well-known suspending agents.

Topical preparations include dusting powders, creams, lotions, gels, and sprays. These various topical preparations may be formulated by well-known procedures. See for example Remington's Pharmaceutical Sciences, Chapter 43, 14th Ed., 1970, Mack Publishing Co., Easton, Pa. 18042, USA.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or table itself or it can be the appropriate number of any of these packaged forms.

The quantity of active compound in a unit dose of preparation may be varied or adjusted from 50 mg to 500 mg according to the particular application and the potency of the active ingredient.

In therapeutic use as anticholinergic and antiemetic agents the compounds utilized in the pharmaceutical method of this invention are administered at the initial dosage of about 0.1 mg to about 50 mg per kilogram. A dose range of about 0.5 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), N,N-dimethylacetamide, suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by sterilization accomplished by filtering. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in unit dosage form for ease of administration and uniformity of dosage. Unit dosage form as used herein refers to physically discrete units suitable as unitary dosages for the mammalian subjects to be treated; each unit containing a predetermined quantity of the active material calculated to produce the desired therapeutic effect in association with the required pharmaceutical carrier. The specification for the novel unit dosage forms of the invention are dictated by and directly dependent on (a) the unique characteristics of the active material and the particular therapeutic effect to be achieved, and (b) the limitation inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in unit dosage form as hereinbefore disclosed. A unit dosage form can, for example, contain the principal active compound in amounts ranging from about 0.1 to about 500 mg/ml of carrier. In the case of compositions containing supplementary active ingredients, the dosages are determined by reference to the usual dose and the manner of administration of the said ingredients. The daily parenteral doses for mammalian subjects to be treated ranges from 0.1 mg/kg to 100 mg/kg. The preferred daily dosage range is 0.3 mg/kg to 10 mg/kg.

The invention and the best mode of practicing the same are illustrated by the following examples of preferred embodiments of selected compounds and their preparation and of pharmaceutical compositions comprising the compounds.

EXAMPLE 1

Compound 1; Morpholine, 4-[2-[4-(diphenylmethylene)-1-piperidinyl]ethyl], dihydrochloride A mixture of ethyl isonipecotate (7.85 g, 0.05 mole, N-(2-chloroethyl)morpholine hydrochloride (9.30 g, 0.05 mole) and sodium bicarbonate (12.0 g, 0.14 mole) inEtOH (250 ml) was stirred at room temperature for two hours and at reflux temperature for three hours. The reaction mixture was filtered, concentrated and the residue extracted with Et₂O. The Et₂O layer was concentrated to give 13.4 g (quantitative yield) of 4-piperidinecarboxylic acid, 1-[2-(4-morpholinyl)-ethyl]-, ethyl ester, NMR (CDCl₃) 4.0 (t, 2H), 3.6 (m, 4H), 3.0–2.3 (m, 13H), 2.2–1.5 (m, 4H), 1.4–1.0 (t, 3H).

This oil was dissolved in Et₂O (50 ml) and added dropwise to an ice-cooled 2M phenyllithium solution in Et₂O (150 ml, 0.30 mole). After stirring for one hour the ice-bath was removed and stirring continued at room temperature for an additional 1.5 hours. The reaction mixture was poured onto a mixture of ice and water; the ether layer separated, dried (Na₂SO₄) and evaporated to give 30.10 g of product.

This product, alpha-4-piperidinemethanol, 1-[2-(4-morpholinyl)ethyl]-alpha,alpha-diphenyl-, obtained as an oil, was dissolved in 10 percent HCl (about 100 ml), the solution refluxed for one hour, and the resulting white precipitate separated by filtration. The solid was suspended in boiling Et₂O and filtered while hot. In this manner, 22.91 g (77 percent) of morpholine, 4-[2-[4-(diphenylmethylene)-1-piperidyl]ethyl]-, dihydrochloride, was obtained as white solid. Analytical sample was prepared by recrystallization from EtOH-H₂O; mp 285 (dec).

Following the same procedure there was obtained:
Compound 2; Piperidine, 4-(diphenylmethylene)-1-[2-(1-pyrrolidinyl)ethyl]-, dihydrochloride;
Compound 3; Piperidine, 4-(diphenylmethylene)-1-[2-(1-piperidinyl)ethyl]-, dihydrochloride, hydrate (4:1);
Compound 4; Piperidine, 4-(diphenylmethylene)-1-[3-(1-piperidinyl)propyl]-, dihydrochloride, hemihydrate;
Compound 5; Piperidine, 4-(diphenylmethylene)-1-[2-(1-methyl-2-pyrrolidinyl)ethyl]-, dihydrochloride, hemihydrate.

Further, following the same procedure, one can obtain compounds as follows:
Thiomorpholine, 4-methyl-3-[[4-[phenyl[3-(trifluoromethyl)-phenyl]methylene]-1-piperidinyl]methyl]-;
Piperazine, 2-[2-[4-(diphenylmethylene)-1-piperidinyl]ethyl]-4-ethyl-1-methyl-;
Piperazine, 1-[3-[4-(diphenylmethylene)-1-piperidinyl]propyl]-4-phenyl-;
Piperidine, 1-[3-[4-(diphenylmethylene)-1-piperidinyl]propyl]-2-methyl;
Piperidine, 2-[[4-(diphenylmethylene)-1-piperidinyl]methyl]-1-(phenylmethyl)-5-propyl-;
Quinoline, 1-[2-[4-(diphenylmethylene)-1-piperdinyl]ethyl]-1,2,3,4-tetrahydro-;
1H-Indole, 2-[[4-(diphenylmethylene)-1-piperidinyl]methyl]-1-(4-fluorophenyl)-2,3-dihydro-;
Phenol, 3-[1-[3-[4-(diphenylmethylene)-1-piperidinyl]propyl]-3-piperidinyl]-;
Pyridine, 2-[2-[4-(Diphenylmethylene)-1-piperidinyl]ethyl]-4-(4-fluorophenyl)-1,2,3,6-tetrahydro-1-propyl-;
1H-Benzimidazole, 1-[2-[4-(diphenylmethylene)-1-piperidinyl]ethyl];
Isoquinoline, 2-[3-[4-(diphenylmethylene)-1-piperidinyl]propyl]-1,2,3,4-tetrahydro-; and
1H-Indole, 1-[[4-(diphenylmethylene)-1-piperidinyl]ethyl]octahydro-.

EXAMPLE 2

Compound 7; Quinoline, 1-[3-[4-(diphenylmethylene-1-piperidinyl]-1-oxopropyl]-1,2,3,4-tetrahydro-, monohydrochloride, hydrate (4:1)

To a stirred, ice-cooled, solution of ethyl isonipecotate (78.5 g, 0.50 mole) and triethylamine (200 ml, 1.4 mole) in CHCl₃ (1000 ml), triphenylmethyl chloride (15.33 g, 0.55 mole) was added. After stirring overnight at room temperature, the reaction mixture was washed with H₂O, dried (Na₂SO₄) and the solvent evaporated. The oily residue was crystallized from MeOH—CHCl₃, yielding 108.19 (96 percent) of 4-piperidine carboxylic acid, 1-(triphenylmethyl)ethyl ester as a white solid; mp 154°–155° C.

A solution of this ester (14.49 g, 0.036 mole) in Et₂O (200 ml) was added dropwise into an ice-cooled solution of 2.2M phenyllithium in Et₂O (150 ml, 0.33 mole). After stirring at ice-bath temperature for one hour and at room temperature for two hours, the reaction mixture was poured into a mixture of ice and water. The ether layer was separated, dried (Na₂SO₄), and the solvent evaporated to give a white solid. This was suspended in boiling pentane and the insoluble solid collected by filtration to give 17.42 (95 percent) of 4-piperidinemethanol, alpha,alpha-diphenyl-1-(triphenylmethyl)-hydrate (4:1); mp 238°–240° C.

A suspension of 4-piperidinemethanol, alpha,alpha-diphenyl-1-(triphenylmethyl)-, hydrate (4:1) (5.09 g, 0.09 mole) in 10.0 percent HCl (about 100 ml) was heated at reflux temperature for one hour. A clear solution followed by precipitation of a reddish solid took place. After refluxing for one hour, the reaction mixture was allowed to cool to room temperature. A heavy white precipitate separated. Et₂O was added with vigorous stirring and the insoluble white solid separated by filtration to give 2.58 g (91 percent) of 4-diphenylmethylene piperidine hydrochloride, mp 286°–288° C.

A mixture of piperidine, 4-diphenylmethylene (2.49 g, 0.01 mole), 1-(3-chloro-1-oxopropyl)-1,2,3,4-tetrahydroquinoline (2.24 g, 0.01 mole) and sodium bicarbonate (2.3 g, 0.027 mole) in EtOH (100 ml), was refluxed for 24 hours, cooled, filtered, and concentrated to give an oil. This was extracted with Et₂O which upon treatment with ethanol-HCl deposited 2.72 g (57 percent) of quinoline, 1-[3-[4-(diphenylmethylene)-1-piperidinyl]-1-oxopropyl]-1,2,3,4-tetrahydro-, monohydrochloride, hydrate (4:2); mp 175°–178° C.

Following the same procedure there was obtained:
Compound 8; Pyridine, 1-[3-[4-(diphenylmethylene-1-piperidinyl]-1-oxopropyl]-4-(fluorophenoxy)-1,2,3,6-tetrahydro-, 2-hydroxy-1,2,3-propane tricarboxylate(1:1), dihydrate; mp; 100° C. (dec).
The free base was purified by column chromatography (silica) before formation of the salt.
Compound 9; 2-Cyclohexen-1-one, 3-[[2-[4-(diphenylmethylene)-1-piperidinyl]ethyl]amino]-5,5-dimethyl; mp 171°–172° C.

EXAMPLE 3

Compound 10; Quinoline, 1-[3-[4-(diphenylmethylene)-1-piperidinyl]propyl]-1,2,3,4-tetrahydro-, dihydrochloride, monohydrate A mixture of quinoline, 1-[3-[4-(diphenylmethylene)-1-piperidinyl]-1-oxopropyl]-1,2,3,4-tetrahydro, monohydrochloride, hydrate (4:1) (2.22 g, 0.0051 mole) and lithium aluminum hydride (0.60 g, 0.0153 mole) in THF was refluxed for five hours. Excess LiAlH$_4$ was decomposed by careful addition of H$_2$O. This was filtered, most of the THF evaporated and the remaining aqueous layer extracted with CHCl$_3$. After drying (K$_2$CO$_3$), the CHCl$_3$ was evaporated and the resulting oil dissolved in EtOH and treated with HCl gas. The oily precipitate was crystallized from EtOH to give 1.7 g (67 percent) of the product; mp 110° C. (dec).

EXAMPLE 4

Compound 11; 4,4-Piperidinediol, 1-[3-[4-(diphenylmethylene)-1-piperidinyl]-1-oxopropyl]

A solution of pyridine, 1-[3-[4-(diphenylmethylene)-1-piperidinyl]-1-oxopropyl]-4-(4-fluorophenoxy)-1,2,3,6-tetrahydro-, (2.9 g) in Et$_2$O (about 50 ml) was shaken with 10 percent aqueous HCl (100 ml). The aqueous layer was separated, neutralized with 10 percent aqueous NaOH, and extracted with CHCl$_3$. The CHCl$_3$ layer was dried (K$_2$CO$_3$) and concentrated to give an oil. This, upon trituration with ether, gave 1.24 g (51 percent) of the product; mp 108°–110° C.

EXAMPLE 5

Compound 12; 4-Piperidinol, 1-[3-[4-(diphenylmethylene)-1-piperidinyl]propyl]-,dihydrochloride, hemihydrate To an ice-cooled and stirred solution of diphenylmethylene piperidine hydrochloride (4.5 g, 0.016 mole) and triethylamine (3.18 g, 0.0314 mole) in ether (100 ml), a solution of 3-chloropropionyl chloride (1.99 g, 0.016 mole) in Et$_2$O (50 ml) was added dropwise. After stirring at room temperature overnight, the reaction mixture was refluxed for 0.5 hours, cooled, and filtered. The filtrate was washed with 10 percent aqueous HCl, 10 percent aqueous NaOH and water successively, dried (Na$_2$SO$_4$) and concentrated to give a white solid. This was triturated with pentane to give 2.75 g (52 percent) of piperidine, 1-(3-chloro-1-oxopropyl)-4-(diphenylmethylene). Recrystallization from Et$_2$O gave a solid; mp 103.5°–104° C.

Anal calcd for C$_{19}$H$_{22}$NClO: C, 74.21; H, 6.53; N, 4.12; Cl, 10.43, Found: C, 75.32; H, 6.72; N, 4.11; Cl, 9.21.

This was used in the next step without further purification.

A mixture of piperidine, 1-(3-chloro-1-oxopropyl)-4-(diphenylmethylene) (3.39 g, 0.01 more), 4-hydroxypiperidine (1.01 g, 0.01 mole) and sodium bicarbonate (2.52 g, 0.03 mole) in EtOH (75 ml) was refluxed for 16 hours; filtered, and the filtrate concentrated. The residue was extracted with hot Et$_2$O and the solvent evaporated to give 4-(diphenylmethylene-1-[3-(4-hydroxy-1-piperidinyl)-1-oxopropyl]piperidine as an amorphous solid. This was employed in the next step without further purification.

The solid was dissolved in THF containing LiAlH$_4$ (1.6 g) and refluxed for five hours. Excess LiAlH$_4$ was destroyed by careful addition of H$_2$O. Et$_2$O was added, the organic layer separated, dried (K$_2$CO$_3$), and the solvent removed to give 3.56 g (85 percent) of 4-piperidinol, 1-[3-[4-(diphenylmethylene)-1-piperidinyl]propyl], dihydrochloride, hemihydrate. A solution of the free base in Et$_2$O was treated with Et$_2$O-HCl, yielding 3.19 g (63 percent) of the hydrochloride salt; mp 267 (dec).

Following the same procedure there was obtained:

Compound 13; 4-Piperidineethanol, 1-[3-[4-(diphenylmethylene)-1-piperidinyl]propyl]-,dihydrochloride, monohydrate; mp 115° C.

Compound 20; Piperidine, 4-(diphenylmethylene)-1-[1-oxo-4-(1-piperidinyl)butyl]-; from piperidine, 1-(4-chloro-1-oxobutyl)-4-(diphenylmethylene), (6.26 g, 0.018 mole) and piperidine (60 ml, used as solvent) as pale orange solid, yield; 4.33 g (60 percent), mp 125°–127° C.

Anal calcd for C$_{27}$H$_{34}$N$_2$O: C, 80.55; H, 8.51; N, 6.96. Found: C, 80.69; H, 8.62; N, 6.91.

The piperidine, 1-(4-chloro-1-oxobutyl)-4-(diphenylmethylene), was prepared from diphenylmethylene piperidine (20 g, 0.70 mole) and 4-chlorobutyryl chloride (3.92 g, 0.035 mole) in Et$_2$O, yield 5.15 g (42 percent); mp 82°–86° C.

Anal calcd for C$_{22}$H$_{24}$ClNO: C, 74.66; H, 6.84; N, 3.96. Found: C, 74.64; H, 6.89; N, 3.88.

Compound 6; Piperidine, 4-(diphenylmethylene)-1-[4-(1-piperidinyl)butyl]-, dihydrochloride; mp 299°–301° C.

EXAMPLE 6

Compound 14; Piperidine, 1-[3-(1-piperidinyl)propyl]-4-[bis-(4-fluorophenyl)-methylene]-, dihydrochloride, hydrate (2:1)

To an ice-cooled p-fluorophenyl magnesium bromide Grignard reagent prepared from Mg (13.86 g, 0.57 mole) and p-fluorobromobenzene (100 g, 0.57 mole) in Et$_2$O (250 ml), a solution of N-tritylethylisonipecotate (Example 2) (22.77 g, 0.051 mole) in Et$_2$O (450 ml) was added dropwise with stirring. After stirring at ice-bath temperature for one hour, and room temperature overnight, the reaction mixture was refluxed for one half hour and poured into ice-H$_2$O mixture. The Et$_2$O layer was separated, dried, (Na$_2$SO$_4$) and the solvent removed to give a gummy solid. This was extracted with hot pentane and the insoluble residue dried under high vacuum to give 26.88 g (86 percent) of 4-piperidinomethanol, alpha-bis-(4-fluorophenyl)-1-(triphenylmethyl) as an amorphous white solid. Analytical sample was obtained by recrystallization from heptane; mp 90° (turns to glass). The product gives a single spot on TLC, silica-variety of eluents.

Anal calcd for C$_{37}$H$_{33}$NF$_2$O.½H$_2$O: C, 80.12; H, 6.18; N, 2.53. Found: C, 80.45; H, 6.40; N, 2.52.

A solution of 4-piperidinemethanol, alpha,alpha-bis-(4-fluorophenyl)-1-(triphenylmethyl) (16.0 g, 0.029 mole) in 50 percent aqueous acetic acid (150 ml) was refluxed for one hour; cooled to room temperature and the precipitated trityl alcohol (quantitative yield) was separated by filtration. The filtrate was concentrated and the resulting oily residue was dissolved in CHCl$_3$, washed with aqueous NaHCO$_3$, dried (Na$_2$SO$_4$), to give 4-phenylpiperidinemethanol, alpha,alpha-bis-(4-fluorophenyl) as an oil; IR (CHCl$_3$): 3700 cm$^{-1}$ and 3620 cm$^{-1}$ (OH-stretch).

This, without further purification, was dissolved in aqueous 10 percent HCl (100 ml) and refluxed for one hour, cooled to room temperature, and extracted with CHCl$_3$ after neutralization with aqueous NaOH. The CHCl$_3$ layer was dried (Na$_2$SI$_4$) and the solvent evaporated to give 5.72 g (69 percent) of piperidine, 4-[bis-(4-fluorophenyl)methylene] as an oil. A portion of this was cleaned by column chromatography (alumina-CHCl$_3$) to give an oil which solidified upon high vacuum suction; mp 95° (turns to glass). The other portion was dissolved in Et₂O and treated with Et₂O-oxalic acid, depositing the oxalate salt as a white solid. This was washed with pentane and recrystallized from EtOAc-Et₂O; mp 210 (dec).

Anal calcd for $C_{18}H_{12}NF_2$: C, 75.77; H, 6.01; N, 4.91. Found: C, 75.05; H, 6.00; N, 4.91.

Anal calcd for $C_{18}H_{17}NF_2.(CO_2H)_2$: C, 61.06; H, 5.38; N, 3.56. Found: C, 61.59; H, 5.13; N, 3.71.

A mixture of piperidine 4-[bis-(4-fluorophenyl)-methylene] (2.86 g, 0.01 mole), N-(3-chloropropyl)-piperidine hydrochloride (1.98 g, 0.01 mole) and sodium bicarbonate (3.36 g, 0.04 mole) in EtOH (100 ml) was refluxed for six hours, filtered, and the solvent evaporated. The oily residue was extracted with CHCl₃, filtered, and concentrated. The resulting oil was dissolved in EtOH, treated with HCl gas, and the solvent evaporated to give 4.73 g (quantitative) of piperidine, 1-[3-(1-piperidinyl)propyl]-4-[bis-(4-fluorophenyl)methylene]-, dihydrochloride, hydrate (2:1), as a white solid; mp 284°–287° C.

Following the same procedure there was obtained:

Compound 15; Piperidine, 4-[bis-(4-fluorophenyl)-methylene]-1-[2-(1-piperidinyl)ethyl]-, dihydrochloride; mp 268° C. (dec).

Compound 16; Piperidine, 4-[bis-(4-fluorophenyl)-methylene]-1-[2-(1-methyl-2-pyrrolidinyl)ethyl]-, (E)-2-butanedioate (1:2); mp 163° C. (dec).

Compound 17; Piperidine, 4-[bis-(4-fluorophenyl)-methylene]-1-[3-(1-piperidinyl)propyl]-, dihydrochloride; mp 283° C. (dec).

EXAMPLE 7

Compound 18; Piperidine, 4-[(3-chlorophenyl)phenylmethylene]-1-[3-(1-piperidinyl)propyl]-, dihydrochloride, from piperidine, 4-[(3-chlorophenyl)-phenylmethylene]-, monohydrochloride, and N-(3-chloropropyl)piperidine hydrochloride.

The intermediate piperidine, 4-[(3-chlorophenyl)-phenylmethylene]-, was prepared in accordance with a procedure by G. Cavallini, et al, Farmaco, Ed Sci. 12, 853 (1958) from 4-benzoylpyridine (18.32 g, 0.10 mole) and Mg (2.4 g, 0.10 mole) to give 5.72 g (19 percent) of 4-pyridine-methanol, alpha-(3-chlorophenyl)alpha-phenyl; mp 176°–178° C.

Anal calcd for C, 73.10; H, 4.77; N, 4.74, Found: C, 73.25; H, 4.25; N, 4.70.

Catalytic reduction (H₂/Pt₂O) gave 4-piperidinomethanol, 2-(3-chlorophenyl)-2-phenyl, as a sticky solid. This without further purification was dehydrated to give piperidine, 4-[(3-chlorophenyl)-phenylmethylene]-, monohydrochloride; mp 196°–198° C.

Anal calcd for $C_{18}H_{18}ClN.2HCl$, C, 67.51; H, 5.98; N, 4.37. Found: C, 67.90; H, 6.06; N, 4.44.

Following the same procedure there was obtained:

Compound 19; *Piperidine,* 4-[(3-fluorophenyl)phenylmethylene]-1-[3-(1-piperidinyl)propyl)-, dihydrochloride; mp 299°–304° C.

4-pyrimidine-methanol, alpha-(3-fluorophenyl)alpha-phenyl; mp 192°–194° C. was obtained in 57 percent yield.

Anal calcd for $C_{18}H_{16}FNO$: C, 77.40; H, 5.05; N, 5.01. Found: C, 76.58; H, 5.06, N, 4.88.

Piperidine, 4-[(3-fluorophenyl)phenylmethylene], hydrochloride; mp 258°–260° C., Further, following the same procedure using piperidine, 4-[(3-chlorophenyl)(3-fluorophenyl)-methylene]-, monohydrochloride, and N-(2-chloroethyl)thiomorpholine hydrochloride, one can obtain thiomorpholine, 4-[2-[4-[(3-chlorophenyl)(3-fluorophenyl)-methylene]-1-piperidinyl]ethyl]-.

Anal calcd for $C_{18}H_{18}FN.HCl$: C, 71.16; H, 6.30; N, 4.61. Found: C, 71.02; H, 6.38; N, 4.64.

EXAMPLE 8

Compound 21; Carbamimidothioic acid, N'-cyano-N-[3-[4-(diphenylmethylene)-1-piperidinyl]-propyl]-, methyl ester A solution of piperidine, 4-(diphenylmethylene) (0.10 mole) and acrylamide (8.95 g, 0.062 mole) in EtOH (50 ml) was refluxed overnight. This reaction mixture was filtered and concentrated. The resulting while solid residue was dissolved in CHCl₃, washed with H₂O (3×150 ml), dried (Na₂SO₄) and the solvent removed to give thick yellow oil. Crystallization from CH₂Cl₂-i-Pr₂O afforded 29.01 g (75%) of 1-piperidinepropanamide, 4-(diphenylmethylene)-; mp 105°–7° C.

Anal calcd for $C_{21}H_{26}N_2O$: C, 78.71; H, 7.55; N, 8.76. Found: C, 78.57; H, 7.67; N, 8.69.

To an ice-cooled suspension of LiAlH₄ (10.31 g, 0.27 mole) in THF (100 ml), a solution of 1-piperidinepropanamide, 4-(diphenylmethylene) 29.01 g, 0.091 mole) in THF (100 ml) was added dropwise. After stirring for 0.5 hours, the ice-bath was removed, the reaction mixture refluxed for six hours, quenched (EtOAc and 10% NaOH) and the resulting granular precipitate removed by filtration. The filtrate was concentrated to ca 20 ml, dissolved in CHCl₃, washed with H₂O, and the solvent removed to give a yellow-green oil. This was dissolved in MeOH, treated with HCl gas and the solvent evaporated. The residue crystallized from CH₂Cl₂-Et₂O to give 1-piperidinepropaneamine, 4-(diphenylmethylene)dihydrochloride hemihydrate as white solid in quantitative yield; mp 249°–252° C.

Anal calcd for $C_{21}H_{26}N_2.2HCl.\frac{1}{2}H_2O$: C, 64.44; H, 7.53; N, 7.21. Found: C, 64.75; H, 7.33; N, 7.11.

A solution of 1-piperidinepropaneamine, 4-(diphenylmethylene) (p.033 mole) in Et₂O (30 ml) was added dropwise to a solution of dimethyl cyanocarbonimidodithioate (4.86 g, 0.033 mole) in Et₂O (500 ml). After stirring at room temperature for two hours; the resulting white precipitate was collected by filtration, yielding 5.15 g of carbamimidothioic acid, N'-cyano-N-[3-[4-(diphenylmethylene)-1-piperidinyl]propyl]-methyl ester; mp 161°–164° C.

Compound 22; Guanidine, N'-cyano-N-[3-[4-(diphenylmethylene)-1-piperidinyl]-propyl]-N'-methyl To an ice-cooled solution of MeNH₂ gas (11.50 g) in absolute EtOH, a solution of carbamimidothioic acid, N'cyano-N-[3-[4-(diphenylmethylene)-1-piperidinyl]-propyl]-methyl ester (1.5 g, 0.037 mole) in EtOH and CHCl₃ was added dropwise. After stirring at room temperature for 16 hours, the solvent was removed and the oily residue crystallized from EtOH, yielding 1.23 g (86%) of the product; mp 180°–181° C.

Compound 23; 1-Piperidinecarboximidamine, N'-cyano-N-[3-[4-diphenylmethylene)-1-piperdinyl]-propyl]

A mixture of carbamimidothioic acid, N'-cyano-N-[3-[4-(diphenylmethylene)-1-piperidinyl]propyl]-methyl ester (1.5 g, 0.0037 mole) and piperidine (50 ml) was refluxed for 48 hours. Excess piperdine was removed. Trituration with Et$_2$O of the orange-brown oily residue yielded 0.63 g (39%) of the product as a white solid; mp 139°-144° C.

The following representative examples 9 through 13 are given as illustrative pharmaceutical compositions utilizing different carriers. In these examples, example 9 illustrates the use of the compounds of the invention in injectables suitable for intravenous or other types of injection into the host animal. Example 10 is directed to an oral syrup preparation, Example 11 to an oral capsule preparation and Example 12 to oral tablets. Example 13 is directed to use of the compounds of the invention in suitable suppositories. For example 9 through 13, the ingredients are listed followed by the methods of preparing the composition.

EXAMPLE 9

| INJECTABLES | |
|---|---|
| Example 9a Compound 1 | |
| COMPOUND 1 | 125 mg–500 mg |
| Water for Injection USP q.s. | |

COMPOUND 1 is dissolved in the water and passed through a 0.22 micron filter. The filtered solution is added to ampoules or vials, sealed and sterilized.

| Example 9b Compound 2 | |
|---|---|
| COMPOUND 2 | 125 mg–500 mg |
| Water for Injection USP q.s. | |

Prepared as per Example 9a above.

EXAMPLE 10

| SYRUP | |
|---|---|
| Example 10a Compound 1 | |
| 250 mg active ingredient/5 ml syrup | |
| COMPOUND 1 | 25 g |
| Purified Water USP | 200 ml |
| Cherry Syrup q.s. or | 1000 ml |

COMPOUND 1 is dissolved in the water and to this solution the syrup is added with mild stirring.

| Example 10b Compound 2 | |
|---|---|
| 125 mg active ingredient/5 ml syrup | |
| Compound 2 | 25 g |
| Purified Water USP q.s. or | 200 ml |
| Cherry Syrup q.s. ad | 1000 ml |

Prepared as per Example 10a above.

EXAMPLE 11

| CAPSULES | |
|---|---|
| Example 11a Compound 1 | |
| 50 mg, 125 mg or 250 mg | |
| Compound 1 | 500 g |
| Lactose USP, Anhydrous q.s. or | 200 g |
| Sterotex Powder HM | 5 g |

Combine COMPOUND 1 and the Lactose in a twin-shell blender equipped with an intensifier bar. Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg. 352.5 mg or 705 mg of the blend, respectively, for the 50 mg., 125 mg and 250 mg containing capsules.

| Example 11b Compound 2 | |
|---|---|
| 50 mg, 125 mg or 250 mg | |
| Compound 2 | 500 g |
| Lactose, Anhydrous q.s. or | 200 g |
| Sterotex Powder | 5 g |

Mix and fill as per Example 11a.

EXAMPLE 12

| TABLETS | |
|---|---|
| Example 12 Compound 1 | |
| 50 mg, 100 mg or 250 mg | |
| Compound 1 | 250 g |
| Corn Starch NF | 200.0 g |
| Cellullose, Microcrystalline | 46.0 g |
| Sterotex Powder HM | 4.0 g |
| Purified Water q.s. or | 300.0 ml |

Combine the corn starch, the cellulose and COMPOUND 1 together in a planetary mixer and mix for two minutes. Add the water to this combination and mix for one minute. The resulting mix is spread on trays and dried on a hot air oven at 50° C. until a moisture level of 1 to 2 percent is obtained. The dried mix is then milled with a Fitzmill through a #RH2B screen at medium speed. The Sterotex Powder is added to a portion of the mix and passed through a #30 screen, and added back to the milled mixture and the total blended for five minutes by drum rolling. Compressed tablets of 250 mg. 375 mg and 750 mg respectively, of the total mix are formed with appropriate sized punches for the 50 mg, 125 mg or 500 mg containing tablets.

EXAMPLE 13

| SUPPOSITORIES | | | |
|---|---|---|---|
| Example 13a Compound 1 | | | |
| 125 mg. 250 mg or 500 mg per 3 g | | | |
| Compound 1 | 125 mg | 250 mg | 500 mg |
| Polyethylene Glycol 1540 | 1925 mg | 1750 mg | 1400 mg |
| Polyethylene Glycol 8000 | 825 mg | 750 mg | 600 mg |

Melt the Polyethylene Glycol 1540 and the Polyethylene Glycol 8000 together at 60° C. and dissolve COMPOUND 1 into the melt. Mold this total at 25° C. into appropriate suppositories.

| Example 13b Compound 2 | | | |
|---|---|---|---|
| 125, 250, 500 mg per 3 g | | | |
| Compound 2 | 125 mg | 200 mg | 500 mg |
| Polyethylene Glycol 1540 | 1925 mg | 1750 mg | 1400 mg |
| Polyethylene Glycol | 825 mg | 750 mg | 600 mg |

| -continued |
| --- |
| Example 13b Compound 2 |
| 125, 250, 500 mg per 3 g |
| 8000 |

Prepare as per Example 13a above.

Having thus described our invention, what we claim and desire by Letters Patent to secure are the following:

1. Diphenylmethylene piperidine compounds having in the free base form the formula:

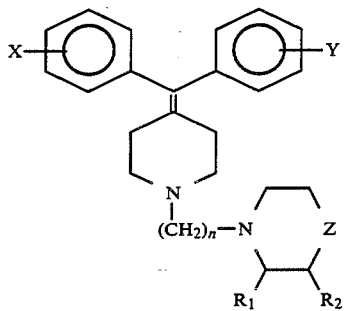

and pharmaceutically acceptable salts thereof, where X and Y, which can be the same or different, are H, halogen, halomethyl, alkyl, or alkoxy; n is 2, 3, or 4; Z is O, $CH_2$, S, single bond, =C-fluorophenoxy, =CHOH, =CHCH$_2$CH$_2$OH, =C(OH)$_2$, or NR$_4$, R$_4$ being H, alkyl, or aryl, and R$_1$ and R$_2$, which can be the same or different are hydrogen, alkyl, or an aromatic or hetero aromatic ring.

2. Compounds according to claim 1 which are:
Piperidine, 4-(diphenylmethylene)-1-[2-(1-pyrrolidinyl)ethyl]-;
Piperidine, 4-(diphenylmethylene)-1-[2-(1-piperidinyl)ethyl]-;
Piperidine, 4-(diphenylmethylene)-1-[3-(1-piperidinyl)propyl]-;
4-Piperidinol, 1-[3-[4-(diphenyl-methylene)-1-piperidinyl]propyl]-;
4-Piperidineethanol, 1-[3-[4-(diphenyl-methylene)-1-piperidinyl]propyl]-;
Piperidine, 4-(diphenylmethylene)-1-[4-(1-piperidinyl)butyl]-;
Piperidine, 1-[3-(1-piperidinyl)propyl]-4-[bis(4-fluorophenyl)methylene];
Piperidine, 4-[bis-(4-fluorophenyl)-methylene]-1-[2-(1-piperidinyl)ethyl]-;
Piperidine, 4-[bis-(3-fluorophenyl)-methylene]-1-[3-(1-piperdinyl)propyl]-;
Piperidine, 4-[4(3-chlorophenyl)phenylmethylene]-1-[3-(1-piperidinyl)propyl]-;
Piperidine, 4-[(3-fluorophenyl)phenylmethylene]-1-[3-(1-piperidinyl)propyl]-; and pharmaceutically acceptable salts thereof.

3. A compound according to claim 1 which is morpholine, 4-[2-[4-(diphenylmethylene)-1-piperidinyl]ethyl]-, and pharmaceutically acceptable salts thereof.

* * * * *